(12) United States Patent
Naatz et al.

(10) Patent No.: US 6,793,889 B2
(45) Date of Patent: Sep. 21, 2004

(54) WIDE-RANGE TOC INSTRUMENT USING PLASMA OXIDATION

(75) Inventors: Ulf W. Naatz, Gelsenkirchen (DE); Yasuo Yamamori, Longmont, CO (US); John Stillian, Longmont, CO (US); Tsutomo Asano, Oita (JP)

(73) Assignee: Hach Company, Loveland, CO (US)

( * ) Notice: Subject to any disclaimer, the term of this patent is extended or adjusted under 35 U.S.C. 154(b) by 358 days.

(21) Appl. No.: 09/928,459

(22) Filed: Aug. 14, 2001

(65) Prior Publication Data
US 2002/0068017 A1 Jun. 6, 2002

Related U.S. Application Data
(60) Provisional application No. 60/224,511, filed on Aug. 14, 2000.

(51) Int. Cl.[7] .............................................. G01N 31/12
(52) U.S. Cl. ........................ 422/80; 422/68.1; 436/39; 436/145; 436/146
(58) Field of Search .......................... 436/39, 106, 114, 436/145, 146

(56) References Cited

U.S. PATENT DOCUMENTS

| 4,626,413 A | 12/1986 | Blades |
| 5,459,075 A | 10/1995 | Fabinski |
| 5,473,162 A | * 12/1995 | Busch et al. ............. 250/341.6 |
| 6,007,777 A | 12/1999 | Purcell |
| 6,114,700 A | 9/2000 | Blades |

OTHER PUBLICATIONS

Bondarowicz, "Total organic carbon analysis by inductively coupled plasma spectroscopy", MS thesis, Roosevelt University (1992).
Haiden Laboratory Co., Ltd., "Plasma generating power source", undated brochure.
Haiden Laboratory Co., Ltd., "Bipolar high–frequency pulse power source", undated brochure.
Korobetskii, et al, "Express method for correction of carbon content determined by standard method", Chem. Abst. 127, 23 (1997), No. 320663t.
Williams, et al, "A Procedure for the simultaneous oxidation of total soluble nitrogen and phosphorus in extracts of fresh and fumigated soils and litters," Chem. Abst. 122, 11 (1995), No. 131955a.

* cited by examiner

*Primary Examiner*—Jill Warden
*Assistant Examiner*—Sam P. Siefke
(74) *Attorney, Agent, or Firm*—Michael de Angeli

(57) ABSTRACT

Total organic carbon in an aqueous or gaseous sample is measured by admitting the sample and an oxidant gas to a cell transparent to plasma, establishing a relatively low energy plasma in the cell, and measuring the $CO_2$ thus produced using FTIR, NDIR, or conductivity-based techniques.

26 Claims, 3 Drawing Sheets

WIDE-RANGE TOC INSTRUMENT USING PLASMA OXIDATION

CROSS-REFERENCE TO RELATED APPLICATION

This application claims priority from Provisional Application Ser. No. 60/224,511, filed Aug. 14, 2000.

FIELD OF THE INVENTION

There are many applications for instruments capable of measuring the total organic carbon content of water (TOC) over a wide range of TOC values. The typical approach is to oxidize the carbon in the sample to carbon dioxide, and measure the latter. For analysis of the TOC of samples of relatively high purity, the sample may be exposed to UV energy (i.e. <254 nm), typically provided by a mercury lamp, possibly in the presence of a $TiO_2$ or other catalyst. The conductivity of a static sample (e.g., a sample taken from a process stream of interest and analyzed separately) can be monitored over time during the UV exposure to determine when the reaction is complete. See commonly-assigned U.S. Pat. No. 4,626,413, and others. Such instruments are capable of extremely accurate measurements of the TOC of water samples. However, the oxidation takes considerable time, so that it would be desirable to provide a faster-responding instrument. Furthermore, the relationship of the conductivity of the water sample to its carbon dioxide content is linear only at low concentrations, leading to complexity in analysis of samples of higher $CO_2$ content.

Current wide range TOC analytical processes use reagents and/or catalysts, such as sodium persulfate and phosphoric acid, to oxidize organic compounds in the sample to carbon dioxide, using either UV energy (i.e. <254 nm), typically provided by a mercury lamp, or heat, typically at least 100° C., to effect oxidation. Oxidation times are typically 5 to 15 minutes and reagents have to be replenished frequently. Commonly the resulting $CO_2$ is diffused across a membrane into a sample of ultrapure water, and the conductivity of the latter measured to determine the $CO_2$ content; this technique again becomes increasingly complicated at higher $CO_2$ concentrations.

As mentioned, the oxidation of carbon to $CO_2$ can be stimulated in several ways. An additional variation is in the treatment of the sample. The sample can be held static in an oxidation cell, or the carbon in a flowing stream can be oxidized as it flows through an oxidation cell. In the latter case, the conductivity is commonly measured at the entry into and exit from the cell, so as to provide a measure of the change in conductivity and thus of the amount of $CO_2$ formed. However, this technique can provide an accurate measure of TOC only if the reaction is completed or is completed to a known degree while the sample is in the cell; neither can be reliably assured.

In a non-catalyzed oxidation process, the sample is typically contained in a platinum crucible and heated to a high temperature, such as 600° C. to 900° C. The $CO_2$ generated is usually measured by means of a NDIR instrument.

As mentioned, the conductivity of a water sample is usually measured to determine the $CO_2$ content and thus measured its TOC. Other conventional $CO_2$ detection techniques employ non-dispersive infrared (NDIR) or Fourier-transform infrared (FTIR) techniques. In another prior art technique, exemplified in publications by Bondarowicz and by Roehl and Hoffman, plasma-stimulated emission is used to measure the $CO_2$ content. The TOC is oxidized by conventional means, and a RF-generated inductively coupled plasma (ICP), typically providing plasma temperatures of >2000° C., is used to heat the resulting carbon to a temperature sufficient to emit radiation; an emission spectrometer is then used to measure the carbon content, and this value is used to determine the TOC.

In a second known technique, exemplified in a paper by Emteryd et al., an ICP is used to simultaneously oxidize the TOC to $CO_2$ and to heat it to a temperature suitable for emission spectrometry.

In both cases, the plasma generated is too hot to allow direct physical attachment of a conventional $CO_2$ detector (e.g., one employing non-dispersive infrared (NDIR), Fourier-transform infrared (FTIR), or conductivity-based techniques), limiting the analytical technique to non-contact optical techniques, such as analysis of the spectral emission or mass spectrometry. This is because the previously described plasmas are "equilibrium" plasmas, that is, in which the energy of the electrons of the plasma is in equilibrium with the rotational and translational energy of the gas molecules. Accordingly, the plasma is physically extremely hot.

The present invention also employs plasma oxidation techniques in connection with the measurement of the TOC of a gaseous sample or a sample of water, but does so in a significantly different way than in these two prior art techniques.

More specifically, it would be desirable to employ plasma oxidation as the technique for converting TOC in the sample to $CO_2$, so as to obtain an instrument capable of analyzing widely-varying TOC contents, yet allowing accurate analytical techniques such as NDIR, FTIR, or conductivity-based techniques to be used to measure the $CO_2$ thus produced.

OBJECTS OF THE INVENTION

It is therefore an object of the invention to provide a wide-range TOC analytical instrument employing plasma oxidation to convert the carbon in a sample to $CO_2$, but doing so at temperatures sufficiently low to allow preferred techniques to be employed for measuring the $CO_2$ thus produced, and doing so in a short time, so as to increase the efficiency of the instrument.

Other objects of the invention will be apparent from the following.

SUMMARY OF THE INVENTION

According to the invention, a dielectric barrier discharge (DBD), also known as a silent discharge (SD) or atmospheric pressure glow discharge (APGD), is provided to oxidize TOC in a gaseous or aqueous sample to $CO_2$. DBDs are characterized by the presence of one or more insulating dielectric layers in the current path between metal electrodes in addition to the discharge gap. As known to those of skill in the art, the microdischarges generated in a DBD can be described as a weakly ionized, non-equilibrium plasma; in this connection, "non-equilibrium plasma" means that the mean energy of the electrons within the plasma is not in equilibrium with the vibration, rotation or translation energy of the bulk gas molecules. Therefore, the majority of the gas molecules stay at ambient temperatures while the electron energy is relatively high, so that the electrons of the plasma are effective in cleaving molecular bonds and thus driving the oxidation of TOC.

The DBD employed according to the present invention is referred to herein simply as "the plasma". Table 1 lists some characteristic microdischarge properties in air at atmospheric pressure for a suitable plasma having a discharge gap of 1 mm (taken from literature).

TABLE 1

| Duration: | $10^{-9}$–$10^{-8}$ s | total charge: | $10^{-10}$–$10^{-9}$ C |
|---|---|---|---|
| Filament radius: | about $10^{-4}$ m | electron density: | $10^{20}$–$10^{21}$ m$^{-3}$ |
| Peak current: | 0.1 A | mean electron energy: | 1–10 eV |
| Current density: | $10^6$–$10^7$ Am$^{-2}$ | filament temperature: | close to gas temperature in the gap |

As noted, the relatively low plasma temperature (that is, as compared to the plasmas discussed in the art cited above) of less than 50° C. allows confinement of the plasma in a glass cell; however, since the plasma is non-equilibrated, as noted the mean electron energy in this type of discharge is still sufficient to cleave chemical bonds. This allows the plasma to be used to drive the oxidation, while permitting measurement of the $CO_2$ thus generated by NDIR, FTIR, or conductivity-based techniques, thereby satisfying an important aspect of the invention.

More specifically, due to their suitable energy, the electrons in the plasma are capable of generating highly reactive species. The nature of these species mainly depends on the type of gas that is filling the discharge gap. In the case of oxygen, some of these species are excited oxygen, atomic oxygen, ozone, peroxides, etc. In particular, in the presence of water (vapor) and oxygen, large quantities of hydroxyl radicals are formed in high amounts responsive to the plasma discharge. Hydroxyl radicals are very strongly oxidizing, and are considered to be the main oxidizing species not only in DBD induced oxidation reactions but also in the photocatalytic oxidation reactions employing UV irradiation of an aqueous sample, as discussed above. Accordingly, in addition to other factors, the available amount of hydroxyl radicals determines the rate of oxidation. The more hydroxyl radicals are generated, the faster the oxidation of a certain sample will proceed. In addition, a DBD also causes the emission of UV light which in turn drives the oxidation process.

According to the invention, the sample can be injected directly into the plasma chamber, and the chamber can be directly coupled to the $CO_2$-detecting analytical instrument with no loss of sample. Thus, highly accurate detectors such as NDIR or FTIR instruments can be used to measure the $CO_2$ content and thus determine the TOC of the sample.

More specifically, as known to those of skill in the art, FTIR provides analysis for numerous compounds, and is thus useful in the experimental stage, so as to ensure that complete oxidation is taking place; in an appropriate production environment (as discussed further below), NDIR, which is specific for a single infrared absorbing substance (here $CO_2$), may be preferred. Under certain circumstances, conductivity-based techniques may be preferred.

Still more specifically, the present invention provides for gas-phase plasma oxidation as well as for plasma oxidation of TOC in a gaseous or aqueous sample to $CO_2$. Creation of the plasma requires only a supply of oxygen-containing gas, such as air, $CO_2$-free air, synthetic air, an inert gas (i.e. helium, argon, xenon etc.) charged with oxygen, or pure oxygen, and application of high voltage electrical power. If the oxidation takes place in the gas phase in the energetic plasma, oxidation times are less than one minute. If the oxidation takes place in the liquid phase, oxidation times are usually longer, but are still typically less than two minutes, thus fulfilling the object of the invention for a fast-responding, wide range instrument. The explanation for the difference in oxidation times is that the active species, which are generated mainly in the gas phase or on the liquid surface of the sample, must diffuse into the liquid phase before the oxidation can take place. To hasten this process, a large surface area is favorable and therefore a large wettable glass surface is provided. The experiments of the present inventors, as summarized below, indicate that plasma-induced oxidation according to the invention is considerably faster than and applicable to a wider range of TOC contents than existing methods.

Detection can be accomplished with any conventional $CO_2$ detection system, such as non-dispersive infrared (NDIR) or Fourier-transform infrared (FTIR) spectroscopy, or by dissolving the $CO_2$-containing gaseous product in a sample of ultrapure water, and measuring the change in conductivity of the water sample; the $CO_2$ content of the sample can be determined from the change in conductivity. Alternatively, the emission spectra of $CO_2$ resulting from the organic carbon oxidation can be measured directly; the intensity of the emission is a function of the concentration of $CO_2$ present.

BRIEF DESCRIPTION OF THE DRAWINGS

The invention will be better understood if reference is made to the accompanying drawings, in which.

DESCRIPTION OF THE PREFERRED EMBODIMENTS

Figure 1:
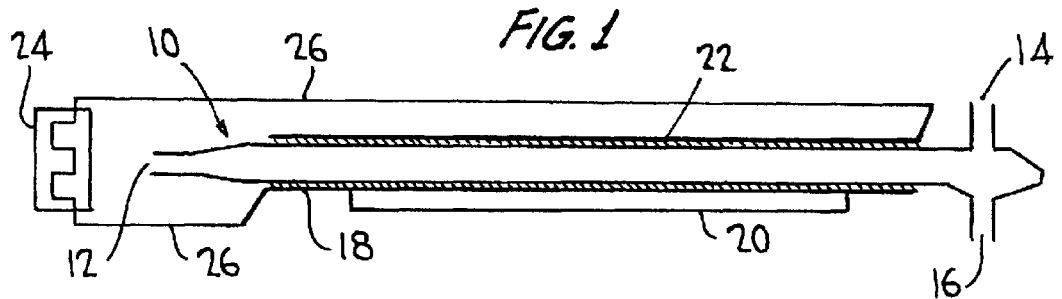
FIG. 1 shows a plan view of a first embodiment of the plasma reactor cell according to the invention in which a mixture of a gaseous sample and the oxidant gas are introduced to the cell through the same inlet.
Figure 2:
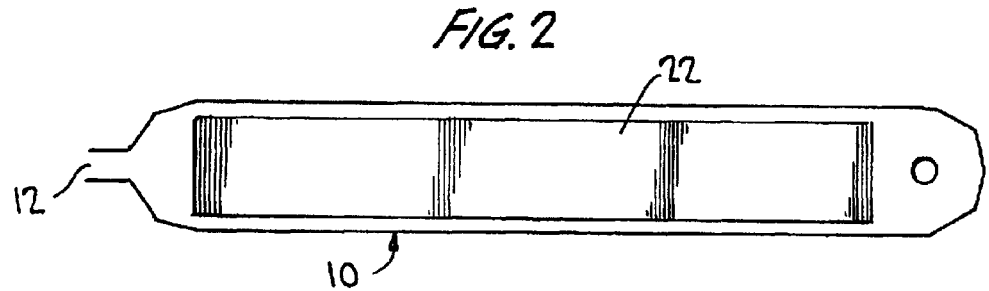
FIG. 2 shows an elevational view of the cell of FIG. 1.
Figure 3:
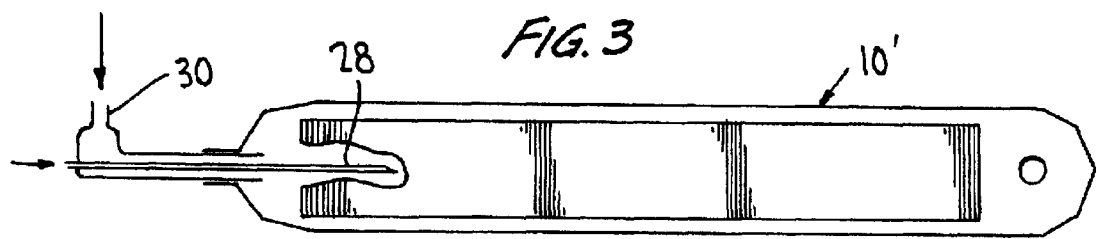
FIG. 3 shows a view similar to FIG. 2 of a second embodiment of the plasma reactor cell, in which a fused silica capillary is implemented as the liquid sample injection device, and an oxygen-containing gas is introduced to the cell separately.
Figure 4:
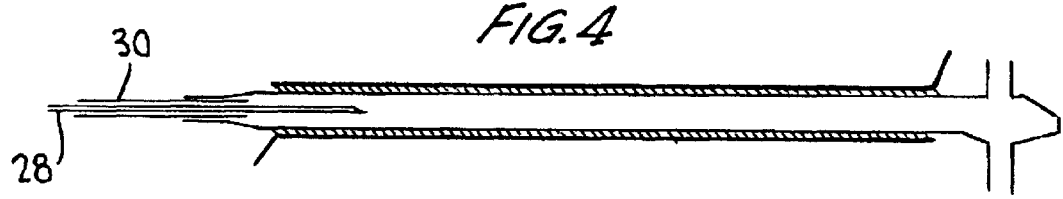
FIG. 4 is a view similar to FIG. 1 of the cell in the FIG. 3 embodiment.

The essential elements of the plasma reactor cell are simply a vessel for containing the sample and the oxidant gas, a pair of electrodes across which a potential can be applied, so as to generate the plasma, and a suitable power supply. FIGS. 1 and 2 show one embodiment of the plasma reactor cell 10 in which the plasma is generated according to the invention, and in which the plasma oxidizes the sample to $CO_2$, while FIGS. 3 and 4 show a second, closely related alternative embodiment. In both embodiments, the cell 10 principally comprises a 13.0 cm×2.15 cm×0.55 cm (outside dimensions) elongated flat rectangular chamber made of borosilicate or quartz glass. The top and bottom glass walls form dielectric layers and have a wall thickness of less than 1 mm. The other walls of the cell 10 are approximately 3 mm thick. Accordingly, the glass walls define an inner volume of approximately 12.4 cm×1.55 cm×0.3 cm (=5.8 ml). The inner glass surface is etched by an HF solution to improve surface wettability. An inlet port 12 and first and second outlet ports, 14 and 16 respectively, are provided at opposite ends of the cell. First and second outlet ports 14 and 16 function as a simple gas/liquid separator.

Two metal electrodes, one referred as ground electrode 18 and the other as high voltage electrode 22, are attached to opposite sides of cell 10. The electrodes are of similar design and are attached similarly. Thus, ground electrode 18 is a 10.5 cm×1.55 cm×0.04 cm copper plate attached to the center of the bottom glass wall by electrically conductive silver grease such that it is at least coextensive with the entire inside transverse dimension of the volume of cell 10. Each of the four edges of the electrode 18 is sealed against the glass surface and the air with a high dielectric polymer paste (TV Corona Dope) to avoid arcing that might be caused by the sharp shaped edges of the electrodes when a high voltage is applied and to prevent ambient air from entering any gap that might otherwise exist between the outer glass wall surface and the electrode surface. Although the gas inside the plasma remains at nearly ambient temperatures, the metal electrodes may heat up during plasma operation. In fact, elevated temperatures might be advantageous in terms of efficient generation of the plasma. However, in the case of a liquid-phase oxidation, vaporization of the aqueous sample must be avoided. Therefore, a cooling device, shown schematically at 20 (i.e., a thermoelectric cooler or a forced air cooler) is also attached to the ground electrode 18 to maintain it at a moderate temperature, e.g., in the range of 15° C. to 60° C., during operation. As noted, a high voltage electrode 22 of the same construction and dimensions is attached in the same way to the center of the top glass wall, and may similarly be supplied with a cooling device. The electrodes 18 and 22 are connected to a high voltage power supply 24 supplied by Haiden Laboratory Co. Ltd., Hyogo, Japan, as indicated at 26.

As will be appreciated by those of skill in the art, when the power supply is energized, an electric field is generated between the electrodes, and a plasma is established inside the cell, that is, between the dielectric surfaces formed by the oppsed elongated flat walls of the cell. Of course, other cell designs could be employed, such as the concentric designs shown in the provisional application from which this application claims priority.

As noted above, the cell 10 in the embodiment of FIGS. 1 and 2 has a single inlet port 12, and is employed where a gaseous sample, e.g., a gaseous mixture of volatile organics, possibly including water vapor, and oxidant gas are mixed prior to supply to the cell. The otherwise similar embodiment 10 of FIGS. 3 and 4 is used where a liquid sample is to be subjected to plasma oxidation. In the liquid case, it is critical for achieving fast and complete oxidation to form a thin and even film of the sample liquid on the inner glass surface. In the design of FIGS. 3 and 4, the liquid sample is sprayed through the capillary 28 onto the bottom glass surface with sufficient hydraulic pressure, i.e. by means of a sample pump, to achieve a thin and uniform film of the sample liquid on the inside surface of the cell. In this case, the oxidant gas is introduced through a separate inlet port 30, concentric with tube 28, so that the sample and the oxygen containing gas are combined in the cell 10.

More specifically, FIGS. 1 and 2 represent a first embodiment of the plasma cell 10, suitable for the determination of TOC in gaseous samples. For example, the apparatus could be employed as a "Breathalyzer" for the measurement of alcohol in one's bloodstream as follows, with reference to FIG. 5, discussed further below. Imagine a gaseous sample of ethanol (e.g., the ethanol contained in one's breath after a couple of beers) in the sample flask 60. Ethanol is a volatile organic compound. Pump 62 would draw the gas to be tested (i.e., a breath sample) through the sample loop 50. Pump 62 is then turned off and pump 54 is turned on, transferring the content of the sample loop 50 through inlet port 12 into the plasma cell 10. The oxidant gas is recirculated through the gas loop 49 containing pump 44, condenser 46 and detector 48. $CO_2$ which is contained in the sample before the plasma oxidation can either be removed prior to oxidation, or the existing $CO_2$ contained in the sample may be measured and taken as the background. Meanwhile pump 54 can also be used to recirculate the sample gas through a second "liquid loop" comprising outlet 16, the sample loop 50, and inlet port 12; however, after the gaseous sample has been successfully introduced from the sample loop 50 into the cell, further recirculation through sample loop 50 is unnecessary, so it could be bypassed if desired. After introduction of the gaseous sample into the cell, the ethanol will be oxidized by the plasma to $CO_2$. The formation of the $CO_2$ is monitored through the course of the oxidation and the end point determined. As there is no liquid phase in this case, there is no need for an injection device such as the capillary 28 employed in the FIGS. 3 and 4 embodiment. A simple "tee" fitting can be employed to combine the sample flow and the oxidant gas flow prior to injection.

FIGS. 3 and 4 describe a second embodiment 10 of the cell, suitable for liquid samples. In principle, there are two different methods for introducing a liquid sample into the plasma cell. Option 1: injecting the liquid sample from the sample loop directly through the capillary 28 into the cell, i.e. by using pump 54 to apply a sufficient hydraulic pressure. The sample and the separately introduced oxidant gas are mixed within the cell. Option 2: Combining the liquid sample from the sample loop with the oxidant gas flow prior to injection. In this case, suction from the oxidant gas flow driven by pump 44 (FIG. 5) aspirates the liquid sample into the cell. Both methods are adequate. In the former case, where the liquid is introduced by capillary 28, the capillary 28 extends into the interior of the cell and reaches into the plasma area to ensure that all of the sample comes into close and immediate contact with the plasma.

Broadly speaking, the apparatus is operated as follows (with reference to FIG. 5): In order to initially fill the plasma cell 10 with an oxygen containing gas, a 20 mlmin$^{-1}$ to 200 mlmin$^{-1}$ gas flow from a gas supply is established through the internal volume of the cell. The gas is chosen for ease of generating a plasma and must contain oxygen in some form ($O_2$, $O_3$, $H_2O_2$, $NO_2$) sufficient to completely oxidize the full amount of organic molecules present in the sample to $CO_2$. For example, air, which typically contains 78% v/v $N_2$, 21% V/V $O_2$ and 0.03% V/V $CO_2$, is adequate for most applications, if it is stripped of $CO_2$ before admission to the plasma oxidation chamber. Accordingly, in the experimental arrangement shown in FIG. 5, air is admitted at 40 to a column 42 filled with soda lime, for absorbing all $CO_2$ from the ambient air. The stream of oxidant air is passed through a water filled flask 43, to remove dust particles from the soda lime column and to saturate the air stream with water vapor, and a flowmeter 45. $N_2$ with $O_2$ added at from 1% to 20% is also acceptable. It has been determined that the presence of water or water vapor in the sample does not affect the plasma negatively.

Figure 5:
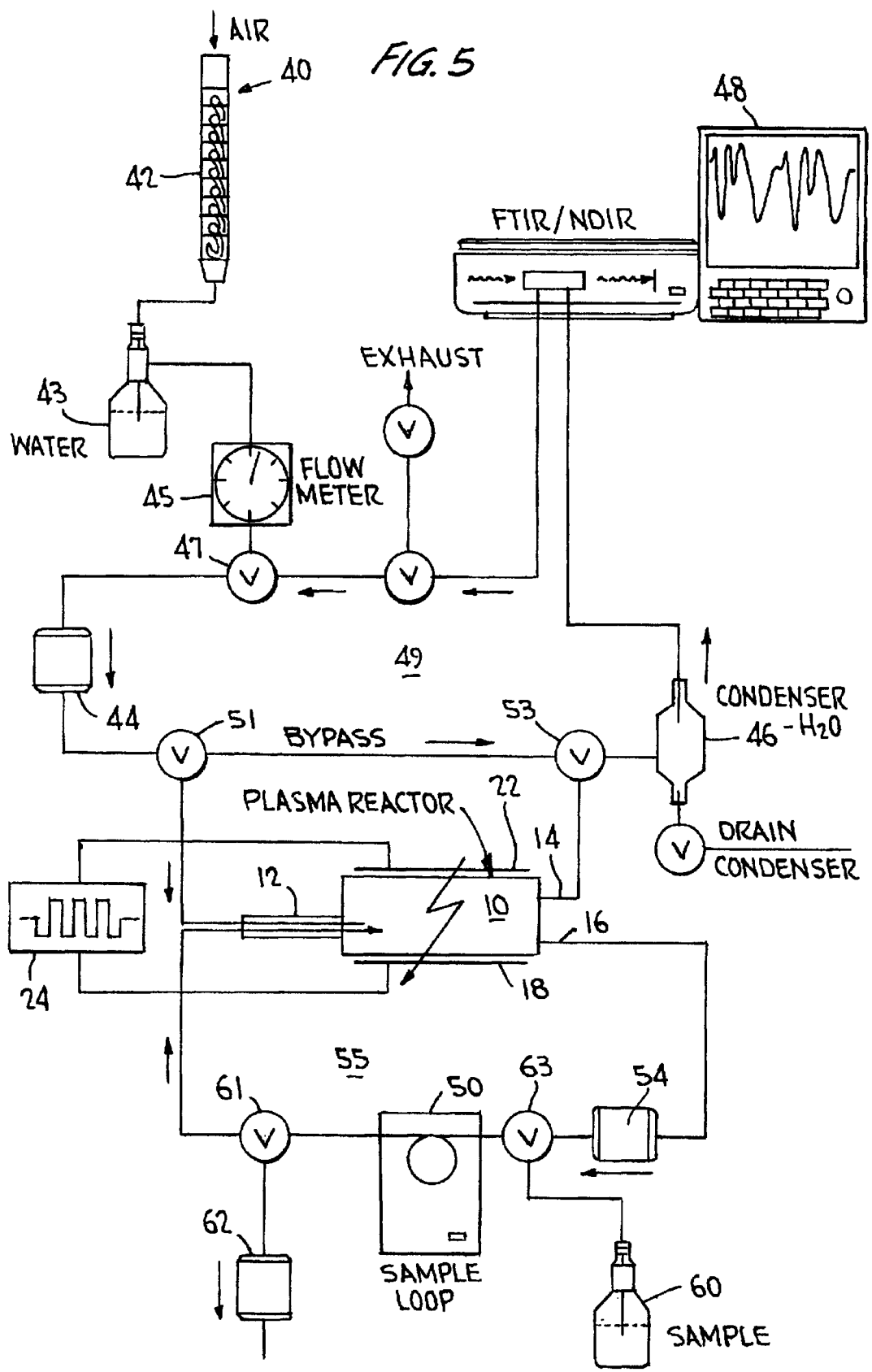
FIG. 5 shows a typical experimental arrangement according to the invention.

Gas flow through the passage can be maintained continuous by supply of the oxidant gas, or the gas present in the cell can be circulated in a "gas loop" 49 by means of a pump 44. The latter arrangement is shown in FIG. 5; the gas outlet port 14 is connected to the inlet port 12 through a loop 49 which contains the pump 44, a condenser 46 and a $CO_2$ detector device 48. Condenser 46 is employed to avoid the undesirable condensation of water inside the $CO_2$ detector cell. Condensation can be avoided either by cooling the gas stream beneath its dew point at the operating temperature of the detector, e.g., by means of a thermoelectric cooler or ice trap, or by passing the gas stream by a water-selective membrane, such as Nafion. The amount of oxygen trapped inside the volume of the plasma cell and associated loop, i.e., after closing of valve 47, is sufficient to completely oxidize the full amount of carbon present in the sample.

High frequency, high voltage electrical power, specifically pulsed square wave alternating DC at frequency of between 1 kHz and 10 kHz and a voltage of between 6 kV and 12 kV, is then applied to the cell by power supply 24. As mentioned above, the "Plasma Generating Power Source" offered by Haiden Laboratory Company of Hyogo, Japan is preferred. A plasma is established in the cell, as evidenced by an increase in current and a visible homogeneous or filamentary blue violet glow from the plasma cell. After ignition, the voltage is accordingly decreased to maintain the power applied at 0.08 kW to 0.25 kw. This is considered a relatively low-energy non-equilibrium plasma, that is, as compared to the high-energy equilibrium plasmas used according to the prior art to stimulate $CO_2$ in a sample to radiation-emitting temperatures; typical power levels for the plasmas used for these purposes are 0.5 to 2 kW. Such high-energy plasmas would be unsuitable in practice of the present invention, as they would render the sample far too hot to be analyzed using the preferred techniques.

At the low power levels employed in the plasma according to the invention, a liquid sample stays liquid, i.e., an aqueous sample is not vaporized, as would occur if a high-temperature plasma were employed, as in certain of the prior art referred to above. Therefore, simple vertically-spaced exit ports 14 and 16 are sufficient to separate the oxidant gas, containing an increasing amount of $CO_2$ as the TOC is oxidized, from the liquid. The $CO_2$-containing oxidant gas in the gas loop 49 can be repetitively recirculated through the detector 48 and the cell 10, while the liquid sample can remain static within cell 10 or be similarly recirculated through a liquid loop 55.

More specifically, after establishment of the proper flow of the oxidant gas stream, and establishment of the plasma, an aqueous or gaseous sample of known volume is introduced into the cell 10 for oxidation. The sample can be drawn from a flask 60 into a sample loop 50, e.g., a PTFE tube of an appropriate and known volume, fitted with valves 61 and 63 on either side, so as to define a known volume of sample, or the sample can simply be injected by a syringe inserted though a septum. Sample introduction can be performed either intermittently or continuously, and can be achieved by a sample introduction device that sprays the sample into the gas stream feeding the plasma (such as a pneumatic, ultrasonic, or other type of nebulizer) or by a glass capillary that reaches into the plasma area and distributes the sample evenly on the inner glass surface to form a liquid film. Since the ground electrode is kept at ambient temperatures, vaporization of a liquid sample is avoided. The sample is driven through the plasma towards the opposite end of the cell either by the gas flow itself (in the case of a gas or aerosol) or by gravity if the cell is mounted in an angle to the horizontal.

The TOC in the sample is oxidized to $CO_2$ by the plasma. The $CO_2$ generated is measured at the outlet of the plasma cell 10 by a detector 48 using FTIR, NDIR or another suitable detection means. In a preferred embodiment, the oxidant gas, including increasing quantities of $CO_2$, is passed through cell 10 repeatedly until an unchanging value for the $CO_2$ content as measured by detector 48 indicates that oxidation is complete. More specifically, a gas loop indicated at 49 and including pump 44, detector 48, and condenser 46, is defined by proper settings of valves 47, 51, and 53. By admitting a known quantity of sample into the cell 10, and circulating the product gas stream through the detector 48 and back into the cell by way of loop 49, the $CO_2$ generation can be monitored through the course of the oxidation process. All of the generated $CO_2$ is captured within this gas loop. Therefore, the end point of the oxidation process can easily be determined, since the $CO_2$ concentration in the gas stream will reach a plateau value at the end of the oxidation. The final $CO_2$ concentration in the gas stream can be correlated to the initial carbon content of the sample. If the product gas is not circulated, that is, if the $CO_2$ containing product gas is discharged after $CO_2$ detection, the detected $CO_2$ signal must be somehow integrated over time to calculate the TOC, i.e. by an electronic integrator.

Similarly, as noted, the liquid remaining after each oxidation cycle may be withdrawn at the outlet port 16 by means of a pump 54 and reinjected into the plasma cell 10 in order to ensure complete oxidation. Thus employing a "liquid loop" 55 is preferred in many cases, since it ensures that all of the TOC in the sample will eventually reach the plasma oxidation cell 10.

As noted, oxidation is determined to have been completed when recirculation of the oxidant gas (as well as recirculation of the liquid sample, if this step is performed) does not result in detection of additional amounts of $CO_2$, i.e., when the measured value for the $CO_2$ stabilizes. Thus determining precisely when the reaction is complete is functionally equivalent to selecting a static sample from a stream and monitoring its conductivity in a cell during simultaneous exposure to UV, and determining that the reaction is complete when the conductivity reaches a final value, i.e., as practiced according to the commonly-assigned patents referred to above. Thus, if a "liquid loop" 55 is employed, the same stream of sample flows through the plasma cell 10 repeatedly, so that the oxidation will be completed. This "closed-loop" practice is to be distinguished from the common prior art practice of passing a stream through a UV exposure cell, and measuring the conductivity before and after exposure; under such circumstances there is no guarantee that the oxidation is completed, calling the TOC results derived therefrom into doubt.

Table 2 below shows some typical results of a series of experiments carried out using the apparatus as described above to measure the TOC of samples containing various organic compounds. The results compare the volume of $CO_2$ generated by oxidation of the listed compound, as measured by FTIR, to the amount of $CO_2$ theoretically generated by complete oxidation of a known amount of the compound mentioned as injected into the system. As shown by the column headed "$CO_2$ recovery in percent", these results illustrate that volatile compounds such as ethanol as well as non-volatile compounds such as benzoic acid are completely oxidized to $CO_2$; that is, no detectable starting material, intermediate compounds, or carbon monoxide remains after oxidation. In addition, the amount of detected $CO_2$ correlates well to the carbon content of gaseous calibration samples within the experimental error level. Samples can be introduced in liquid or gas form, most commonly as a sample of water with organic contamination to be determined, as in traditional TOC analyzers.

TABLE 2 experimental results

| compound | m.w./gmol$^{-1}$ b.p/° C. | sample conc./molL$^{-1}$ | injected volume/μl | inj. sample contains mol of compound | inj. sample contains mol of carbon | theor. volume $CO_2$/cc after oxidation | measured vol. after oxidation/ cc | $CO_2$ recovery in percent | analysis time/ sec |
|---|---|---|---|---|---|---|---|---|---|
| methanol | 32.0 64.7 | 0.74 | 10 | 7.39*10$^{-6}$ | 7.39*10$^{-6}$ | 0.18 | 0.17 | 95 | 90 |
| ethanol | 46.1 78.5 | 1.41 | 10 | 1.41*10$^{-5}$ | 2.84*10$^{-5}$ | 0.68 | 0.65 | 95 | 90 |
| 1-propanol | 60.1 97.7 | 0.76 | 10 | 7.58*10$^{-6}$ | 2.28*10$^{-5}$ | 0.56 | 0.54 | 96 | 90 |
| 1-butanol | 74.0 117 | 0.71 | 10 | 7.11*10$^{-5}$ | 2.83*10$^{-5}$ | 0.69 | 0.66 | 95 | 120 |
| 1-pentanol | 88.0 138 | 0.11 | 10 | 1.13*10$^{-6}$ | 5.63*10$^{-6}$ | 0.14 | 0.13 | 97 | 120 |
| phenol | 94.1 182 | 0.24 | 10 | 2.7*10$^{-6}$ | 1.62*10$^{-5}$ | 0.40 | 0.38 | 95 | 120 |
| benzoic acid | 122.1 249 | 0.023 | 10 | 2.34*10$^{-7}$ | 1.64*10$^{-6}$ | 0.040 | 0.037 | 94 | 120 | ideal gas: $pV = nRT$ $R = 8.31441$ Jmol$^{-1}$K$^{-1}$; $T = 298.16$ K; $p = 1.01325*10^5$ Pa; $RT/p = 0.0245$ m$^3$mol$^{-1}$ and $[J] = $ m$^2$kgs$^{-2}$ $[Pa] = $ kgm$^{-2}$s$^{-2}$
plasma parameters: 7 kV, 5 kHz, 0.08–0.25 kW
amount of oxygen: 6 cc of oxygen at 1 atm.: 2.5*10$^{-4}$ mol
experimental error: +/– 10%

The selection of the instrument 48 used to measure the $CO_2$ in the sample, i.e., whether this should be an FTIR, NDIR, or conductivity-based instrument, is relatively complex, and the instrument chosen will likely vary from case to case.

In Fourier Transform Infrared Spectroscopy (FTIR), a source of wide bandwidth radiation is used to produce light over a broad range of infrared wavelengths. An interferometer and a detector determine the intensity of absorption as a function of the interferometer position. By applying a Fourier Transformation, an intensity vs. wavenumber plot is generated that is responsive to the IR absorption spectrum. In NDIR, the absorption is measured over all the relevant wavelengths, so that the specific absorption at the corresponding specific wavelength is not determined. Therefore, the spectral resolution of FTIR is superior over the unspecific NDIR measurement. FTIR accordingly provides excellent results, and is capable of differentiating $CO_2$ from other species likely to be present, e.g., $N_2O$, but instruments employing FTIR principles are costly and much too bulky for production use.

An NDIR instrument such as described in commonly-assigned U.S. Pat. No. 6,114,700, which measures the amount of infrared radiation passing through the gas in the cell of the instrument, provides very accurate measurements, and is compact and inexpensive. However, this instrument is not suitable if the oxidant gas includes nitrogen, i.e., if air is used, as $N_2O$ will be formed in the plasma and cannot be distinguished by this instrument from $CO_2$. A company known as "Sensors Europe" offers an NDIR instrument said to be capable of distinguishing $CO_2$ from $N_2O$ and to prevent cross interference in the determination process; if true, this instrument might be useful in connection with implementation of the present invention when it is desired to use air as the oxidant.

Finally, conductivity-based techniques for determining the concentration of $CO_2$ in a sample of water by measuring its conductivity are well-known. However, such techniques are linear only at low levels of $CO_2$, at which the $CO_2$ is in dissociated ionic form; at higher concentrations, some of the $CO_2$ remains in solution and does not contribute to the conductivity. Accordingly, if conductivity-based techniques are to be used to measure the $CO_2$, attention must be paid to the overall TOC concentration range.

Other aspects of the system design shown in FIG. 5 will be apparent to those of skill in the art. In the experimental arrangement shown, the sample to be tested is supplied in a flask 60; for the initial filling of the sample loop 50, a stream of sample from the flask 60 is drawn by pump 62 through the sample loop 50 and through the pump 62 into a drain. When pump 62 is shut off, the sample loop 50 contains a defined and reproducible amount of sample. A further pump 54 is provided to transfer the sample into the cell 10 through inlet port 12.

Some TOC-containing samples of interest will also comprise an initial concentration of inorganic carbon (TIC), normally in the form of carbonate. The "total carbon" concentration (TC) of such samples as measured after plasma oxidation as above, if performed in the presence of oxygen- and nitrogen-containing gases, such as air, will be responsive to the sum of the $CO_2$ responsive to the inorganic carbon, plus the $CO_2$ created due to the oxidation of organic compounds in the sample. More specifically, $NO_2$ will be generated in the plasma due to reaction of oxygen with the nitrogen in the air. The $NO_2$ then dissolves in the aqueous sample (or reacts with OH radicals present) during the plasma oxidation, generating acidic $HNO_3$, and the $HNO_3$ acidifies the sample, liberating the $CO_2$ from the carbonates. Accordingly, $CO_2$ will be detected responsive to the TIC in the sample.

Therefore, in order to obtain an accurate measurement of TOC alone, as is often desired, the inorganic carbon must be removed from the sample or its concentration measured prior to oxidation in the plasma. The TIC can be removed from the sample prior to exposure to the plasma by acidifying the sample, liberating the $CO_2$ as above, and passing the acidified sample past one side of a $CO_2$-selective membrane having ultrapure water on its other side, to remove the inorganic carbon as $CO_2$, or by treatment with an anion exchange bed to remove the carbonate. In either case, the $CO_2$ generated via subsequent oxidation in the plasma is due only to the TOC in the sample.

Figure 6:
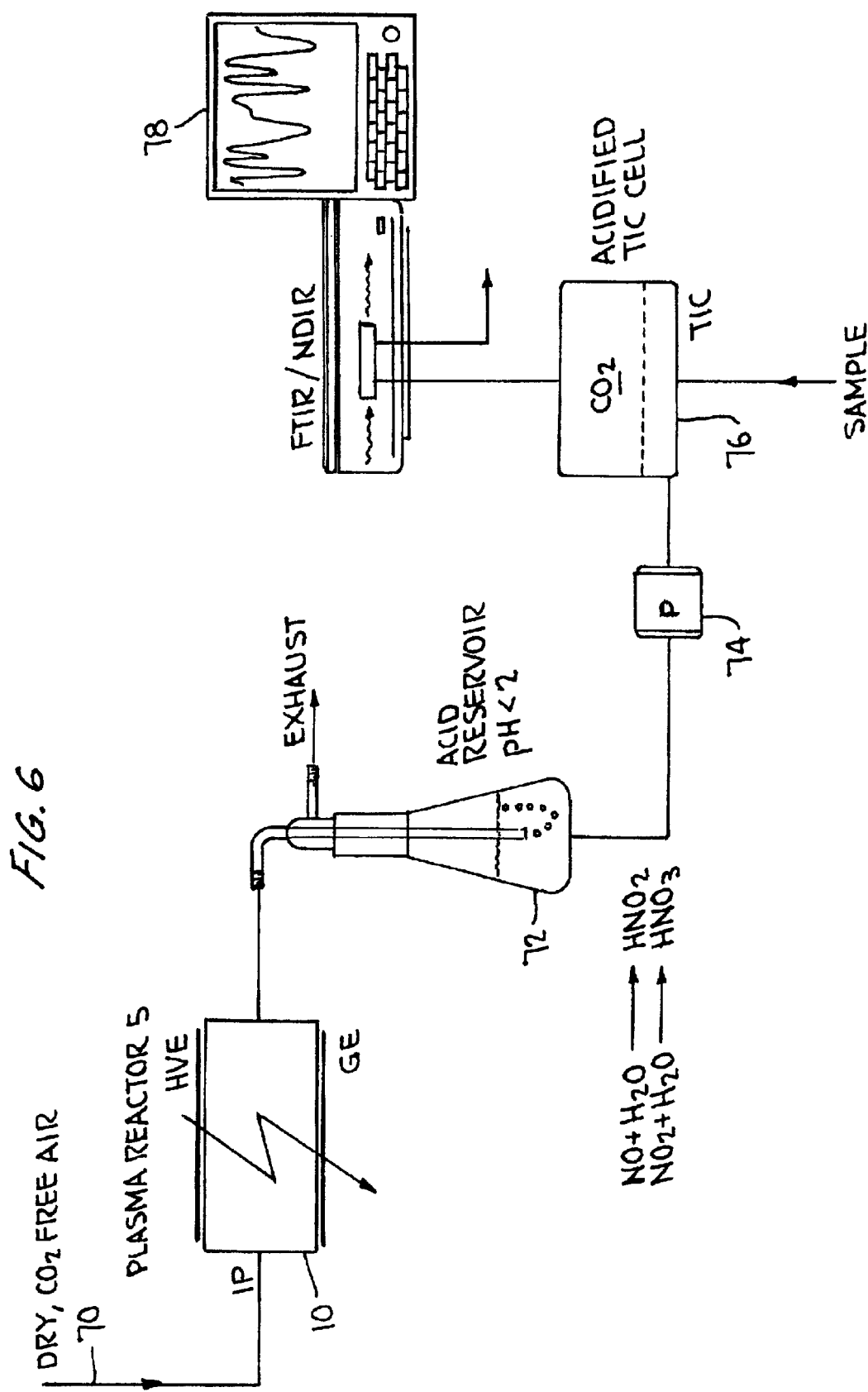
FIG. 6 shows a further arrangement wherein the apparatus is also used to measure the total inorganic carbon (TIC) of the sample.

FIG. 6 shows a partial reconfiguration of the FIG. 5 system that may be useful in order that the previously described plasma cell can also be used to produce an acidic aqueous solution, which can in turn be used to acidify a sample for the purpose of removing or measuring its TIC. For this purpose, dry, $CO_2$-free air from a source indicated at 70 is subjected to plasma conditions in plasma cell 10, and the product gas stream is bubbled through a flask 72 filled with ultrapure water. The $NO_2$ formed in the gas stream (as above) generates a $HNO_2/HNO_3$ solution which easily reaches a pH<2. By this procedure the instrument can produce and replenish its own acid supply, which may be very convenient in certain circumstances. For subsequent TIC measurement, a pump 74 mixes a portion of the acid from the acid reservoir with an aliquot of the sample in a TIC cell. At a pH <4 all of the carbonates in the sample will be transformed to $CO_2$ which can be measured by a $CO_2$ detector 78, e.g., the same FTIR, NDIR or conductivity-based instrument used later to measure the $CO_2$ content of the sample. In fact, the plasma cell 10 can also serve as the TIC cell 76; that is, the sample is mixed with a portion of the acid inside the non-operating cell 10 while the gas phase is circulated through the cell and the $CO_2$ detector 78. The detector determines the amount of $CO_2$ that is liberated simply due to the acidification of the sample, and this $CO_2$ amount is assigned to TIC. After minor reconfiguration of the apparatus, plasma oxidation of the TIC-free remaining sample can be performed, as above, in order to obtain the accurate TOC value.

While several implementations of and alternative constructions for the instrument of the invention have been disclosed, the invention is not to be limited thereby, but only by the following claims.

What is claimed is:

1. A system for the measurement of the total organic carbon content (TOC) of a sample of water, comprising:
   a. a source of a $CO_2$-free oxidant gas;
   b. a cell of a material capable of containing a plasma, said cell defining an interior volume for receiving said oxidant gas and said sample, being provided with at least one inlet and one outlet port, and comprising first and second electrodes disposed on opposite sides of said cell;
   c. a high voltage power supply connected across said first and second electrodes and operable to cause a low-intensity, non-equilibrium plasma to be formed in said interior volume of said cell, whereby TOG in said sample is oxidized by said oxidant gas to form $CO_2$; and
   d. an instrument for measuring the quantity of $CO_2$ in said cell after exposure of the mixture of said sample and said oxidant to said plasma and oxidation of said TOC thereby to $CO_2$.

2. The system of claim 1, wherein said instrument for measuring the quantity of $CO_2$ in said cell is a Fourier-transform infrared (FTIR) spectroscopic instrument.

3. The system of claim 1, wherein said instrument for measuring the quantity of $CO_2$ in said cell is a non-dispersive infrared (NDIR) instrument.

4. The system of claim 1, wherein said instrument for measuring the quantity of $CO_2$ in said cell measures the conductivity of a quantity of water in which the $CO_2$ produced by oxidation of the TOC is dissolved.

5. The system of claim 1, wherein said cell comprises first and second inlet ports, whereby said oxidant gas is admitted via one inlet port and said sample via the other, whereby said oxidant and said sample are not mixed until both are within said cell.

6. The system of claim 5, wherein said first and second inlet ports comprise coaxial tubes.

7. The system of claim 1, wherein said call defines opposed pairs of parallel, elongated side walls, one pair of opposed walls being substantially wider than the other, so as to define a flat, elongated interior volume.

8. The system of claim 7, wherein said electrodes are disposed on opposed wider walls of said cell.

9. The system of claim 8, wherein said electrodes are sealed to the walls of said cell in gas tight fashion.

10. The system of claim 1, wherein said cell is fabricated of glass or quartz.

11. The system of claim 1, wherein said cell and said instrument for measuring the quantity of $CO_2$ in said cell are connected in a loop.

12. The system of claim 11, wherein said instrument comprises means for monitoring the quantity of $CO_2$ in said cell over time, in order to determine when all of the carbon in said sample has been oxidized to $CO_2$ in said cell.

13. The system of claim 11, wherein said loop comprises a condenser.

14. The system of claim 11, wherein said loop comprises a pump.

15. The system of claim 1, further comprising a sample loop of predetermined fixed volume, to be filled with sample to be analyzed before supply of said sample to said cell.

16. The system of claim 1, wherein said cell is connected in a liquid loop, comprising a pump connecting inlet and outlet ports of said cell, whereby an aqueous sample can be recirculated though said cell until oxidation is complete.

17. A method for measuring the total organic carbon content (TOC) of a sample of water, comprising the steps of:
   providing a plasma oxidation device, comprising a cell capable of containing a plasma, having opposed electrodes on opposed sides of said cell, and defining at least one inlet port and an interior volume;
   admitting said sample of water to said interior volume of said cell;
   admitting a quantity of a $CO_2$-free oxidant gas to said interior volume of said cell;
   applying a high-frequency, high-voltage signal across said electrodes, so as to cause a plasma to form across said electrodes, and TOC in said sample to be oxidized to $CO_2$; and
   determining the amount of $CO_2$ thus formed.

18. The method of claim 17, where said step of determining the amount of $CO_2$ thus formed is performed using Fourier-transform infrared (FTIR) spectroscopic techniques.

19. The method of claim 17, where said step of determining the amount of $CO_2$ thus formed is performed using non-dispersive infrared (NDIR) techniques.

20. The method of claim 17, where said step of determining the amount of $CO_2$ thus formed is performed using conductivity-based techniques.

21. The method of claim 17, wherein said oxidant gas and said sample are mixed external to said cell.

22. The method of claim 17, wherein said oxidant gas and said sample are admitted to said cell by separate inlet ports, whereby they are mixed internal to said cell.

23. The method of claim 17, wherein said oxidant gas is air having had any $CO_2$ removed therefrom.

24. The method of claim 17, comprising the further steps of defining a closed loop including said cell and the instrument employed for said step of determining the amount of $CO_2$ produced, and transferring the result of oxidation of carbon in said sample repeatedly therebetween while monitoring the amount of $CO_2$ in said sample, until said monitoring step indicates that the oxidation of carbon in said sample has been completed.

25. The method of claim 24, comprising the further, step of defining a second liquid loop comprising a pump connected between inlet and outlet ports of said cell, and recirculating an aqueous sample through said cell repeatedly, so as to ensure complete oxidation.

26. The method of claim 17, wherein said power supplied is such that said plasma is a low-energy, non-equilibrium plasma.

* * * * *